United States Patent
Rosenberg et al.

(10) Patent No.: US 11,401,503 B2
(45) Date of Patent: Aug. 2, 2022

(54) METHODS OF GROWING TUMOR INFILTRATING LYMPHOCYTES IN GAS-PERMEABLE CONTAINERS

(71) Applicants: The United States of America, as represented by the Secretary, Department of Health and Human Services, Bethesda, MD (US); Wilson Wolf Manufacturing Corporation, New Brighton, MN (US)

(72) Inventors: Steven A. Rosenberg, Potomac, MD (US); Mark E. Dudley, Washington, DC (US); David Stroncek, Rockville, MD (US); Marianna Sabatino, Los Angeles, CA (US); Jianjian Jin, Clarksburg, MD (US); Robert Somerville, Potomac, MD (US); John R. Wilson, New Brighton, MN (US)

(73) Assignees: The United States of America, as represented by the Secretary, Department of Health and Human Services, Bethesda, MD (US); Wilson Wolf Manufacturing Corporation, New Brighton, MN (US)

( * ) Notice: Subject to any disclaimer, the term of this patent is extended or adjusted under 35 U.S.C. 154(b) by 30 days.

(21) Appl. No.: 16/211,859

(22) Filed: Dec. 6, 2018

(65) Prior Publication Data
US 2019/0345444 A1 Nov. 14, 2019

Related U.S. Application Data

(63) Continuation of application No. 15/375,289, filed on Dec. 12, 2016, now abandoned, which is a continuation of application No. 13/424,646, filed on Mar. 20, 2012, now abandoned.

(60) Provisional application No. 61/466,200, filed on Mar. 22, 2011.

(51) Int. Cl.
| | |
|---|---|
| *C12N 5/078* | (2010.01) |
| *C12N 5/0783* | (2010.01) |
| *A61K 39/00* | (2006.01) |
| *A61K 35/12* | (2015.01) |

(52) U.S. Cl.
CPC ........ *C12N 5/0634* (2013.01); *A61K 39/0011* (2013.01); *C12N 5/0638* (2013.01); *A61K 2035/124* (2013.01); *A61K 2039/5158* (2013.01); *C12N 2501/2302* (2013.01); *C12N 2501/2315* (2013.01); *C12N 2501/515* (2013.01); *C12N 2502/11* (2013.01)

(58) Field of Classification Search
None
See application file for complete search history.

(56) References Cited

U.S. PATENT DOCUMENTS

| | | |
|---|---|---|
| 4,435,508 A | 3/1984 | Gabridge |
| 5,225,346 A | 7/1993 | Matsumiya et al. |
| 6,455,310 B1 | 9/2002 | Barbera-Guillem |
| 6,479,252 B1 | 11/2002 | Barbera-Guillem et al. |
| 6,821,772 B2 | 11/2004 | Barbera-Guillem et al. |
| 6,900,055 B1 | 5/2005 | Fuller et al. |
| 9,567,387 B2 | 2/2017 | Wang et al. |
| 2005/0106717 A1 | 5/2005 | Wilson et al. |
| 2005/0233451 A1 | 10/2005 | Liu et al. |
| 2011/0129923 A1 | 6/2011 | Wilson et al. |
| 2013/0102075 A1 | 4/2013 | Vera et al. |

FOREIGN PATENT DOCUMENTS

| | | |
|---|---|---|
| WO | WO 2010/126766 A1 | 11/2010 |
| WO | WO 2011/072088 A2 | 6/2011 |

OTHER PUBLICATIONS

Avgoustiniatos et al., "Commercially Available Gas-Permeable Cell Culture Bags May Not Prevent Anoxia in Cultured or Shipped Islets," *Transplantation Proceedings*, 40: 395-400, (2008).
Barbera-Guillem et al., "OptiCell Concept for Cell Culture Operations," *Genetic Engineering*, 20 (21): 1-4 (2000).
Bohnenkamp et al., "Bioprocess development for the cultivation of human T-lymphocytes in a clinical scale," *Cytotechnology*, 38: 135-145 (2002).
Dudley et al., "Generation of tumor-infiltrating lymphocyte cultures for use in adoptive transfer therapy for melanoma patients," *J. Immunother.*, 26 (4): 332-342 (2003).
Foster et al., "Large-Scale Expansion of Cytomegalovirus-Specific Cytotoxic T Cells in Suspension Culture," *Biotechnol. Bioeng.*, 85 (2): 138-146 (2004).
Hollyman et al., "Manufacturing validation of biologically functional T cells targeted to CD19 antigen for autologous adoptive cell therapy," *J. Immunother.*, 32 (2): 169-180 (2009) (manuscript).
International Searching Authority (European Patent Office), International Search Report and Written Opinion, issued in PCT/US2012/029744, 14 pages, dated Jul. 6, 2012.
Jensen, "Diffusion in tissue cultures on gas-permeable and impermeable supports," *J. Theor. Biol.*, 56 (2): 443-458 (1976).

(Continued)

*Primary Examiner* — Michail A Belyavskyi
(74) *Attorney, Agent, or Firm* — Leydig, Voit & Mayer (57) ABSTRACT

An embodiment of the invention provides a method of promoting regression of cancer in a mammal comprising obtaining a tumor tissue sample from the mammal; culturing the tumor tissue sample in a first gas permeable container containing cell medium therein; obtaining tumor infiltrating lymphocytes (TIL) from the tumor tissue sample; expanding the number of TIL in a second gas permeable container containing cell medium therein using irradiated allogeneic feeder cells and/or irradiated autologous feeder cells; and administering the expanded number of TIL to the mammal. Methods of obtaining an expanded number of TIL from a mammal for adoptive cell immunotherapy are also provided.

13 Claims, 1 Drawing Sheet

(56) References Cited

OTHER PUBLICATIONS

Jin et al., "Simplified Method of the Growth of Human Tumor Infiltrating Lymphocytes in Gas-permeable Flasks to Numbers Needed for Patient Treatment," *Journal of Immunotherapy*, 35(3): 283-292 (2012).

Johnson et al. "Gene therapy with human and mouse T-cell receptors mediates cancer regression and targets normal tissues expressing cognate antigen," *Blood*, 114 (3): 535-546 (2009).

Kirouac et al., "The systematic production of cells for cell therapies," *Cell Stem Cell*, 3 (4): 369-381 (2008).

Klapper et al., "Single-Pass, Closed-System Rapid Expansion of Lymphocyte Cultures for Adoptive Cell Therapy," *J. Immunol. Methods*, 345 (1-2): 90-99 (2009) (manuscript).

Klapper et al., "Single-pass, closed-system rapid expansion of lymphocyte cultures for adoptive cell therapy," *Journal of Immunological Methods*, 345 (1-2): 90-99, 2009.

Lapteva et al., "Optimization Manufacture of Virus- and Tumor-Specific T Cells," *Stem Cells Int.*, 2011: 1-8 (2011).

Morgan et al., "Cancer regression in patients after transfer of genetically engineered lymphocytes," *Science*, 314 (5796): 126-129 (2006).

Product literature for CLINIcell 250 cell culture cassette (2008).
Product literature for Baxter LIFECELL X-FOLD Culture Bag (1999).
Product literature for Baxter LIFECELL X-FOLD Culture Bag (2000).
Product literature for LUMOX plates (2004).
Product literature for OPTICELL units (2000).
Product literature for PERMALIFE bag (2004).
Product literature for PETAKA cull culture system (2004).
Product literature for SICULTURE bag (1996).
Product literature for Stock VUELIFE Bags (2003).
Product literature for VECTRACELL single use bioreactor system (2002).
Product literature for VECTRACELL bag (2004).
Product literature for VIVASCIENCE petriPERM dish (2003).
Product literature for VUELIFE culture bags (2004).

Root, "Antibody Production in vitro Using Vectra Cell Devices," *BioVectra* (2002).

Sadeghi et al., "Large-scale bioreactor expansion of tumor-infiltrating lymphocytes," *Journal of Immunological Methods*, 364: 94-100 (2011).

Somerville et al., "Clinical scale rapid expansion of lymphocytes for adoptive cell transfer therapy in the WAVE® bioreactor," *Journal of Translational Medicine*, 10(69) (2012).

Tran et al., "Manufacturing of large numbers of patient-specific T cells for adoptive immunotherapy: an approach to improving product safety, composition, and production capacity," *J. Immunother.*, 30 (6): 644-654 (2007).

Tran et al., "Minimally cultured tumor-infiltrating lymphocytes display optimal characteristics for adoptive cell therapy," *J. Immunother.*, 31 (8): 742-751 (2008) (manuscript).

Vera et al., "Accelerated production of antigen-specific T cells for preclinical and clinical applications using gas-permeable rapid expansion cultureware (G-Rex)," *J. Immunother.*, 33 (3): 305-315 (2010).

Wu et al., "Identification of a Novel CD8+CD57+ T-cell Subset in Human Melanoma Exhibiting an Incompletely Differentiated Cytotoxic T Lymphoctye Phenotype," *J. Immunother.*, 32 (9): 985-986 (2009).

Zuliani et al., "Value of large scale expansion of tumor infiltrating lymphocytes in a compartmentalized gas-permeable bag: interests for adoptive immunotherapy," *J. Transl. Med.*, 9 (63), 1-9 (2011).

METHODS OF GROWING TUMOR INFILTRATING LYMPHOCYTES IN GAS-PERMEABLE CONTAINERS

CROSS-REFERENCE TO RELATED APPLICATION

This patent application is a continuation of U.S. patent application Ser. No. 15/375,289, filed Dec. 12, 2016, which is a continuation of U.S. patent application Ser. No. 13/424,646, filed Mar. 20, 2012, now abandoned, which claims the benefit of U.S. Provisional Patent Application No. 61/466,200, filed Mar. 22, 2011, each of which is incorporated by reference in its entirety herein.

STATEMENT REGARDING FEDERALLY SPONSORED RESEARCH AND DEVELOPMENT

This invention was made with Government support under project numbers ZIACL002120-03 and Z01BC010985 by the National Institutes of Health, National Cancer Institute. The Government has certain rights in the invention.

BACKGROUND OF THE INVENTION

Adoptive cell therapy (ACT) using tumor infiltrating lymphocytes (TIL) can lead to positive, objective, and durable responses in cancer patients. However, this therapy can involve sophisticated cell processing techniques and equipment. These procedures have introduced technical, regulatory, and logistic challenges to the successful use of TIL as a biological therapy. Accordingly, there is a need in the art for improved methods for growing TIL for use in adoptive cell therapy.

BRIEF SUMMARY OF THE INVENTION

An embodiment of the invention provides a method of promoting regression of cancer in a mammal comprising obtaining a tumor tissue sample from the mammal; culturing the tumor tissue sample in a first gas permeable container containing cell medium therein; obtaining tumor infiltrating lymphocytes (TIL) from the tumor tissue sample; expanding the number of TIL in a second gas permeable container containing cell medium therein using irradiated allogeneic feeder cells and/or irradiated autologous feeder cells; and administering the expanded number of TIL to the mammal.

Another embodiment of the invention provides a method of obtaining an expanded number of TIL from a mammal for adoptive cell immunotherapy comprising obtaining a tumor tissue sample from the mammal; culturing the tumor tissue sample in a first gas permeable container containing cell medium therein; obtaining TIL from the tumor tissue sample; expanding the number of TIL in a second gas permeable container containing cell medium therein using irradiated allogeneic feeder cells and/or irradiated autologous feeder cells.

Still another embodiment of the invention provides a method of obtaining an expanded number of TIL from a mammal for adoptive cell immunotherapy comprising obtaining a tumor tissue sample from the mammal; obtaining TIL from the tumor tissue sample; expanding the number of TIL in a gas permeable container containing cell medium therein using irradiated allogeneic feeder cells and/or irradiated autologous feeder cells.

Another embodiment of the invention provides a method of promoting regression of cancer in a mammal comprising obtaining a tumor tissue sample from the mammal; obtaining TIL from the tumor tissue sample; expanding the number of TIL in a gas permeable container containing cell medium therein using irradiated allogeneic feeder cells and/or irradiated autologous feeder cells; and administering the expanded number of TIL to the mammal.

DETAILED DESCRIPTION OF THE INVENTION

An embodiment of the invention provides a method of promoting regression of cancer in a mammal comprising obtaining a tumor tissue sample from the mammal; culturing the tumor tissue sample in a first gas permeable container containing cell medium therein; obtaining tumor infiltrating lymphocytes (TIL) from the tumor tissue sample; expanding the number of TIL in a second gas permeable container containing cell medium therein using irradiated allogeneic feeder cells and/or irradiated autologous feeder cells; and administering the expanded number of TIL to the mammal.

The inventive methods provide numerous advantages. For example, methods of promoting regression of cancer and obtaining an expanded number of TIL using gas permeable containers are simpler, less labor-intensive, use less reagents, and can be performed using simpler equipment than procedures using non-gas permeable containers (e.g., T-flasks (e.g., T-175 flasks), bags, and multi-well plates). In addition, gas permeable containers may advantageously protect the cells from microbial contamination more effectively than non-gas permeable containers which may be "open" systems. In addition, methods using gas permeable containers may advantageously reduce the number of containers that are used compared to methods using non-gas permeable containers, thereby reducing the amount of labor necessary to carry out the methods and also reducing the risk of microbial contamination. Thus, producing cells in gas permeable containers may be more suitable for compliance with the current manufacturing practice (cGMP) conditions that are required for, e.g., Phase III clinical trials. Moreover, methods using gas-permeable containers advantageously reduce the final culture volume to lower than that obtained with non-gas permeable containers, which advantageously lowers the incubator capacity required to grow the cells, reduces the amount of reagents (e.g., cell culture medium and additives) necessary to grow the cells, and simplifies the equipment and/or procedures for concentrating and washing the cells. Another advantage of the inventive methods is that the cells may be fed less frequently in gas-permeable containers (e.g., about every three to four days) than in non-gas permeable containers (e.g., every other day), particularly when the cells and/or tumor tissue sample are cultured submerged under at least about 1.3 cm of cell culture medium in a gas permeable container. Moreover, cells in gas permeable containers may be handled less frequently than cells in non-gas permeable containers (e.g., bags), which may minimize disturbance of the tumor fragment and provide more reproducible TIL growth. In addition, one or more aspects (e.g., but not limited to, culturing and/or expanding) of the inventive methods may be automatable. The development of a simpler, less expensive, and less labor-intensive method to generate clinically effective TIL is believed to advantageously aid in the more widespread use of adoptive cell therapy and permit the delivery of therapeutically effective TIL to more patients in a shorter time period. Faster and more efficient adoptive cell therapy may allow patients to be treated more quickly when the disease is at an earlier, less progressive stage, which increases the likelihood that more patients will respond positively to treatment. The inventive methods may also make it possible to treat certain patients who previously may not have been successfully treated because sufficient numbers of TIL were not generated due to the technical and logistical complexities of methods that do not use gas permeable flasks. Accordingly, the inventive methods advantageously may make it possible to treat or prevent a wider variety of cancers and, therefore, treat a larger number of patients.

The method comprises obtaining a tumor tissue sample from the mammal. The tumor tissue sample can be obtained from numerous sources, including but not limited to tumor biopsy or necropsy. The tumor tissue sample may be obtained from any cancer, including but not limited to any of the cancers described herein. Preferably, the cancer is melanoma. The tumor tissue sample may be obtained from any mammal. Preferably, the tumor tissue sample is obtained from a human. In an embodiment, the tumor tissue sample may be a tumor tissue fragment. The tumor tissue sample may be fragmented, e.g., by dissection, to provide a tumor tissue fragment. Alternatively or additionally, the tumor tissue sample may, optionally, be enzymatically or mechanically digested. Suitable enzymes for fragmenting the tumor tissue sample include, but are not limited to, collagenase. In an embodiment, the tumor tissue sample is fragmented without digestion. The tumor tissue fragment may be any suitable size. Preferably, the tumor tissue fragment has a size of about 1 $mm^3$ or less to about 8 $mm^3$ or larger, about 1 $mm^3$ to about 4 $mm^3$, about 1 $mm^3$ to about 2 $mm^3$, or about 1 $mm^3$.

The method further comprises culturing the tumor tissue sample in a first gas permeable container containing cell medium therein. In an embodiment, the tumor tissue sample is cultured directly on the gas permeable material in the gas permeable container without digestion. In another embodiment, an enzymatically or mechanically digested tumor tissue sample may be cultured directly on the gas permeable material. Any suitable cell medium may be used. The cell culture medium may further comprise any suitable T-cell growth factor such as, e.g., interleukin (IL)-2. The cell culture medium may optionally further comprise human AB serum. The tumor tissue sample may contain TIL that are autologous to the patient. Culturing the tumor tissue sample may include culturing the TIL present in the tumor sample.

The method also comprises obtaining TIL from the tumor tissue sample. The tumor tissue sample comprises TIL. As the tumor tissue sample is cultured in the gas permeable container, e.g., on gas permeable material in the container, TIL present in the tumor tissue sample also begin to grow in the gas permeable container, e.g., on the gas permeable material. TIL may be obtained from the tumor tissue sample in any suitable manner.

The first gas permeable container may be any suitable gas permeable container. In an embodiment of the invention, the first gas permeable container comprises a base, sides, and a cap. The container, preferably the base, may comprise a gas permeable support and a gas permeable material, e.g., a gas permeable membrane. The gas permeable material may be positioned inside the container directly on the gas permeable support which comprises openings (e.g., channels) in fluid communication with ambient gas in order to facilitate gas exchange between the interior of the container and the ambient gas. The cap may comprise a vent and/or a port (e.g., an access port). In a preferred embodiment, the access port may have an opening greater than about 1 mm to about 1 cm (e.g., greater than about 1 mm or greater than about 1 cm). An access port with an opening greater than about 1 mm to about 1 cm may advantageously eliminate or reduce disturbance of the TIL. In an embodiment, the gas permeable container may comprise a vent or a vented port, which may be advantageous in the event that the temperature in the container drops during handling. Preferably the first gas permeable container is a gas permeable container as described in U.S. Patent Application Publication No. 2005/0106717, which is incorporated herein by reference, and commercially available from Wilson Wolf Manufacturing Corporation (e.g., G-Rex10, GP200, G-Rex100, GP2000 containers) (New Brighton, Minn.).

The first gas permeable container may have any suitable cell medium volume capacity. For example, the first gas permeable container may have a medium volume capacity of about 40 mL or more; about 200 mL or more; about 500 mL or more; about 2,000 mL or more; or about 5,000 mL or more. Although the first gas permeable container may have any suitable medium volume capacity, the tumor tissue sample and/or TIL may be cultured in any suitable volume of medium. Preferably, the tumor tissue sample and/or TIL are cultured submerged under a height of at least about 1.3 cm of cell culture medium. More preferably, the tumor tissue sample and/or TIL are cultured submerged under a height of at least about 2.0 cm of cell culture medium. Tumor tissue samples and/or TIL cultured on a gas permeable material submerged under a height of at least about 1.3 cm or a height of at least about 2.0 cm of medium may, advantageously, be handled and fed less frequently.

In addition, the first gas permeable container may provide any suitable surface area for the growth of the TIL. For example, the gas permeable container may have a surface area for growth of the TIL of about 10 cm$^2$ or more; about 100 cm$^2$ or more; or about 650 cm$^2$ or more.

In use, the tumor tissue sample and/or TIL are cultured inside the first gas permeable container in contact with the gas permeable material and submerged under a suitable volume of culture medium. Culturing the tumor tissue sample and/or TIL in contact with the gas permeable material facilitates gas exchange between the cells and the ambient air. Facilitating gas exchange between the cells and the ambient air facilitates the respiration, growth, and viability of the cells. Moreover, the gas exchange across the gas permeable material can facilitate circulation of the medium (e.g., by convection and diffusion) within the container, which facilitates feeding of the TIL.

The method further comprises expanding the number of TIL in a second gas permeable container containing cell medium therein using irradiated allogeneic feeder cells and/or irradiated autologous feeder cells. In an embodiment, the number of TIL is expanded using a ratio of about 1 TIL to at least about 20 feeder cells, about 1 TIL to at least about 25 feeder cells, about 1 TIL to at least about 50 feeder cells, about 1 TIL to at least about 100 feeder cells, about 1 TIL to at least about 200 feeder cells, e.g., a TIL-to-feeder cell ratio of about 1 to about 20, about 1 to about 25, about 1 to about 50, about 1 to about 100, or about 1 to about 200. The second gas permeable container may be as described for the first container.

The cultured TIL are expanded, preferably, rapidly expanded. Rapid expansion provides an increase in the number of TIL of at least about 50-fold (or 60-, 70-, 80-, 90-, or 100-fold, or greater) over a period of about 10 to about 14 days, preferably about 14 days. More preferably, rapid expansion provides an increase of at least about 200-fold (or 300-, 400-, 500-, 600-, 700-, 800-, 900-, or greater) over a period of about 10 to about 14 days, preferably about 14 days. Most preferably, rapid expansion provides an increase of at least about 1000-fold over a period of about 10 to about 14 days, preferably about 14 days. Preferably, rapid expansion provides an increase of about 1000-fold to about 2000-fold, e.g., about 1000-fold, about 1500-fold, or about 2,000-fold over a period of about 14 days.

Expansion can be accomplished in the gas permeable container by any suitable method. For example, TIL can be rapidly expanded using non-specific T-cell receptor stimulation in the presence of feeder cells (e.g., irradiated allogeneic feeder cells, irradiated autologous feeder cells, and/or artificial antigen presenting cells (e.g., K562 leukemia cells transduced with nucleic acids encoding CD3 and/or CD8)) and either interleukin-2 (IL-2) or interleukin-15 (IL-15), with IL-2 being preferred. In an embodiment of the method, expanding the number of TIL uses about $1 \times 10^9$ to about $4 \times 10^9$ allogeneic feeder cells and/or autologous feeder cells, preferably about $2 \times 10^9$ to about $3 \times 10^9$ allogeneic feeder cells and/or autologous feeder cells. The non-specific T-cell receptor stimulus can include, for example, about 30 ng/ml of OKT3, a mouse monoclonal anti-CD3 antibody (available from ORTHO-MCNEIL, Raritan, N.J. or MILTENYI BIOTECH, Auburn, Calif.). Alternatively, TIL can be rapidly expanded by, for example, stimulation of the TIL in vitro with an antigen (one or more, including antigenic portions thereof, such as epitope(s), or a cell) of the cancer, which can be optionally expressed from a vector, such as an human leukocyte antigen A2 (HLA-A2) binding peptide, e.g., 0.3 µM MART-1:26-35 (27L) or gp100:209-217 (210M), in the presence of a T-cell growth factor, such as 300 IU/ml IL-2 or IL-15, with IL-2 being preferred. Other suitable antigens may include, e.g., NY-ESO-1, TRP-1, TRP-2, tyrosinase cancer antigen, MAGE-A3, SSX-2, and VEGFR2, or antigenic portions thereof. The in vitro-induced TIL are rapidly expanded by re-stimulation with the same antigen(s) of the cancer pulsed onto HLA-A2-expressing antigen-presenting cells. Alternatively, the TIL can be re-stimulated with, for example, irradiated, autologous lymphocytes or with irradiated HLA-A2+ allogeneic lymphocytes and IL-2, for example.

In an embodiment, expanding the number of TIL may comprise using about 5,000 mL to about 10,000 mL of cell medium, preferably about 5,800 mL to about 8,700 mL of cell medium. In an embodiment, expanding the number of TIL uses no more than one type of cell culture medium. Any suitable cell culture medium may be used, e.g., AIM-V cell medium (L-glutamine, 50 µg/ml streptomycin sulfate, and 10 µg/ml gentamicin sulfate) cell culture medium (Invitrogen, Carlsbad Calif.). In this regard, the inventive methods advantageously reduce the amount of medium and the number of types of medium required to expand the number of TIL.

In an embodiment, expanding the number of TIL may comprise feeding the cells no more frequently than every third or fourth day. Expanding the number of cells in a gas permeable container advantageously simplifies the procedures necessary to expand the number of cells by reducing the feeding frequency necessary to expand the cells.

In an embodiment, the cell medium in the first and/or second gas permeable container is unfiltered. Without being bound to a particular theory, it is believed that particulate serum components present in some cell medium supplements (e.g., AB serum) have little or no detrimental effects on TIL growth. The use of unfiltered cell medium may, advantageously, simplify the procedures necessary to expand the number of cells.

In an embodiment, the cell medium in the first and/or second gas permeable container lacks beta-mercaptoethanol (BME). The absence of BME from the cell medium may be advantageously more compliant with cGMP and, thus, may advantageously make it easier to gain regulatory approval.

In an embodiment, the duration of the method comprising obtaining a tumor tissue sample from the mammal; culturing the tumor tissue sample in a first gas permeable container containing cell medium therein; obtaining TIL from the tumor tissue sample; expanding the number of TIL in a second gas permeable container containing cell medium therein using irradiated allogeneic feeder cells and/or irradiated autologous feeder cells may be about 28 to about 42 days, e.g., about 28 days.

The method comprises administering the expanded TIL to the mammal. The TIL can be administered by any suitable route as known in the art. Preferably, the TIL are administered as an intra-arterial or intravenous infusion, which preferably lasts about 30 to about 60 minutes. Other examples of routes of administration include intraperitoneal, intrathecal and intralymphatic.

Likewise, any suitable dose of TIL can be administered. Preferably, from about $1.0 \times 10^{10}$ TIL to about $13.7 \times 10^{10}$ TIL are administered, with an average of around $5.0 \times 10^{10}$ TIL, particularly if the cancer is melanoma. Alternatively, from about $1.2 \times 10^{10}$ to about $4.3 \times 10^{10}$ TIL are administered.

In addition to TIL, macrophages, monocytes, and natural killer (NK) cells may also be obtained from the tumor tissue sample, cultured, and expanded as described herein for TIL. Accordingly, the method may also comprise administering macrophages, monocytes, and natural killer (NK) cells to the mammal. The inventive methods may also be effective for expanding NK cells.

In an embodiment of the method, a T-cell growth factor that promotes the growth and activation of the TIL is administered to the mammal either concomitantly with the TIL or subsequently to the TIL. The T-cell growth factor can be any suitable growth factor that promotes the growth and activation of the TIL. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL-2. IL-2 is a preferred T-cell growth factor.

In an embodiment of the method, the TIL are modified to express a T-cell growth factor that promotes the growth and activation of the TIL. Suitable T-cell growth factors include, for example, any of those described above. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. Desirably, modified TIL express the T-cell growth factor at high levels. T-cell growth factor coding sequences, such as that of IL-12, are readily available in the art, as are promoters, the operable linkage of which to a T-cell growth factor coding sequence promote high-level expression. In an embodiment, the TIL may be modified to express IL-12 as described in World Intellectual Property Organization Patent Application Publication No. WO 2010/126766, which is incorporated herein by reference.

In some embodiments, it is believed, two cytokines are more effective than a single cytokine, and three cytokines, e.g., IL-2, IL-7 and IL-15, are more effective than any two cytokines. It is believed that IL-15 enhances a tumor-specific $CD8^+$ T-cell response. In this regard, the administration of IL-15-cultured cells with IL-2 (such as a bolus injection) can be particularly efficacious. In another embodiment, TIL modified to express IL-12 may be administered with IL-2 as a bolus injection.

The T-cell growth factor can be administered by any suitable route. If more than one T-cell growth factor is administered, they can be administered simultaneously or sequentially, in any order, and by the same route or different routes. Preferably, the T-cell growth factor, such as IL-2, is administered intravenously as a bolus injection. Desirably, the dosage of the T-cell growth factor, such as IL-2, is what is considered by those of ordinary skill in the art to be high. Preferably, a dose of about 720,000 IU/kg of IL-2 is administered three times daily until tolerance, particularly when the cancer is melanoma. Preferably, about 5 to about 15 doses of IL-2 are administered, with an average of around 8 doses.

TIL can recognize any of the unique antigens produced as a result of the estimated 10,000 genetic mutations encoded by each tumor cell genome. The antigen, however, need not be unique. TIL can recognize one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, preferably the TIL recognize MART-1 (such as MART-1: 26-35 (27L)), gp100 (such as gp100:209-217 (210M)), or a "unique" or patient-specific antigen derived from a tumor-encoded mutation. Other suitable melanoma antigens which may be recognized by TIL can include, but are not limited to, tyrosinase, tyrosinase related protein (TRP)1, TRP2, and MAGE. TIL can also recognize antigens such as, for example, NY-ESO-1, telomerase, p53, HER2/neu, carcinoembryonic antigen, or prostate-specific antigen, for treatment of lung carcinoma, breast cancer, colon cancer, prostate cancer, and the like.

In an embodiment of the method, the TIL are modified to express a T cell receptor (TCR) having antigenic specificity for a cancer antigen, e.g., any of the cancer antigens described herein. Suitable TCRs include, for example, those with antigenic specificity for a melanoma antigen, e.g., gp100 or MART-1. Suitable methods of modification are known in the art. See, for instance, Sambrook and Ausubel, supra. For example, the TIL may be transduced to express a T cell receptor (TCR) having antigenic specificity for a cancer antigen using transduction techniques described in Morgan et al., *Science* 314(5796):126-9 (2006) and Johnson et al. *Blood* 114:535-46 (2009).

The cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer. A preferred cancer is melanoma. A particularly preferred cancer is metastatic melanoma.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Promoting regression of cancer in a mammal may comprise treating or preventing cancer in the mammal. The terms "treat," "prevent," and "regression," as well as words stemming therefrom, as used herein, does not necessarily imply 100% or complete regression. Rather, there are varying degrees of treatment, prevention, and regression of which one of ordinary skill in the art recognizes as having a potential benefit or therapeutic effect. In this respect, the inventive methods can provide any amount of any level of treatment, prevention, or regression of cancer in a mammal. Furthermore, the treatment, prevention, or regression provided by the inventive method can include treatment, prevention, or regression of one or more conditions or symptoms of the disease, e.g., cancer. Also, for purposes herein, "treatment," "prevention," and "regression" can encompass delaying the onset of the disease, or a symptom or condition thereof.

Another embodiment provides a method of obtaining an expanded number of TIL from a mammal for adoptive cell immunotherapy comprising obtaining a tumor tissue sample from the mammal; culturing the tumor tissue sample in a first gas permeable container containing cell medium therein; obtaining TIL from the tumor tissue sample; expanding the number of TIL in a second gas permeable container containing cell medium therein using irradiated allogeneic feeder cells and/or irradiated autologous feeder cells.

The method comprises obtaining a tumor tissue sample from the mammal. The tumor tissue sample may be obtained as described herein with respect to any embodiments of the invention.

The method comprises culturing the tumor tissue sample in a first gas permeable container containing cell medium therein. The tumor tissue sample may be cultured in a first gas permeable container as described herein with respect to any embodiments of the invention.

The method comprises obtaining TIL from the tumor tissue sample. The TIL may be obtained from the tumor tissue sample as described herein with respect to any embodiments of the invention.

The method comprises expanding the number of TIL in a second gas permeable container containing cell medium therein using irradiated allogeneic feeder cells and/or irradiated autologous feeder cells. The number of TIL may be expanded as described herein with respect to any embodiments of the invention.

Still another embodiment of the invention provides a method of obtaining an expanded number of TIL from a mammal for adoptive cell immunotherapy comprising obtaining a tumor tissue sample from the mammal; obtaining TIL from the tumor tissue sample; expanding the number of TIL in a gas permeable container containing cell medium therein using irradiated allogeneic feeder cells and/or irradiated autologous feeder cells. Obtaining a tumor tissue sample from the mammal, obtaining TIL from the tumor tissue sample, and expanding the number of TIL in a second gas permeable container containing cell medium therein using irradiated allogeneic feeder cells and/or irradiated autologous feeder cells may be carried out as described herein with respect to any embodiments of the invention.

The method may further comprise culturing the tumor tissue by any suitable method that facilitates the obtaining of TIL from the tumor tissue sample. In this regard, culturing the tumor tissue may comprise establishing multiple independent cultures, e.g., microcultures. For example, culturing the tumor tissue may comprise culturing tumor fragments in plates, e.g., 24-well plates. In an embodiment, the tumor tissue is cultured without a gas permeable container.

In some embodiments, the method further comprises selecting TIL capable of lysing cancer cells while in other embodiments, the method does not include selecting TIL capable of lysing cancer cells. TIL capable of lysing cancer cells may be selected by identifying TILs having any suitable trait associated with the lysis of cancer cells and/or the regression of cancer. Exemplary suitable TIL traits that may serve as the basis for selecting TILs may include any one or more of IFN-γ release upon co-culture with autologous tumor cells; cell surface expression of one or more of CD8, CD27, and CD28; and telomere length. Without being bound to a particular theory, it is believed that cell surface expression of one or more of CD8, CD27, and CD28 and longer telomere lengths are associated with positive objective clinical responses in patients and persistence of the cells in vivo. Preferably the trait is IFN-γ release upon co-culture with autologous tumor cells. In an embodiment of the invention, selected TIL release about 200 pg/ml or more of IFN-γ upon co-culture with tumor cells.

In some embodiments, selecting TIL capable of lysing cancer cells comprises testing individual cultures for presence of the trait and identifying TIL possessing the trait. Methods of testing cultures for the presence of any one or more of IFN-γ release upon co-culture with autologous tumor cells; cell surface expression of one or more of CD8, CD27, and CD28; and telomere length (longer telomeres being associated with regression of cancer) are known in the art.

Any number of cultures may be selected. For example, one, two, three, four, five, or more cultures may be selected. In embodiments in which two or more cultures are selected, the selected cultures may be combined and the number of TIL expanded in one (or more) gas permeable containers. Preferably, however, in embodiments in which two or more cultures are selected, each selected culture is separately expanded in separate gas permeable containers. Without being bound to a particular theory, it is believed that expanding multiple selected cultures separately advantageously increases lymphocyte diversity for patient treatment.

The method may further comprise expanding the number of TIL in an identified culture in a second gas permeable container containing cell medium therein using irradiated allogeneic feeder cells and/or irradiated autologous feeder cells as described herein with respect to any embodiments of the invention.

Another embodiment of the invention provides a method of promoting regression of cancer in a mammal comprising obtaining a tumor tissue sample from the mammal; obtaining TIL from the tumor tissue sample; expanding the number of TIL in a second gas permeable container containing cell medium therein using irradiated allogeneic feeder cells and/or irradiated autologous feeder cells; and administering the expanded number of TIL to the mammal. Obtaining a tumor tissue sample from the mammal, obtaining TIL from the tumor tissue sample, expanding the number of TIL in a gas permeable container containing cell medium therein using irradiated allogeneic feeder cells and/or irradiated autologous feeder cells, and administering the expanded number of TIL to the mammal may be carried out as described herein with respect to any embodiments of the invention. In some embodiments, the method further comprises selecting TIL capable of lysing cancer cells. The TIL may be selected as described herein with respect to any embodiments of the invention.

The following examples further illustrate the invention but, of course, should not be construed as in any way limiting its scope.

EXAMPLES

Initial TIL Culture

Patients were entered into clinical protocols and signed informed consents that were approved by the Institutional Review Board of the National Cancer Institute prior to tumor resection. TIL were initially cultured from enzymatic tumor digests and tumor fragments (about 1 to about 8 mm$^3$) produced by sharp dissection. Tumor digests were generated by incubation in enzyme media (Roswell Park Memorial Institute (RPMI) 1640, 2 mM glutamate, 10 mcg/mL gentamicine, 30 units/mL of DNase and 1.0 mg/mL of collagenase) followed by mechanical dissociation (GentleMACS™ dissociator, Miltenyi Biotec, Auburn, Calif.). In brief, immediately after placing the tumor in enzyme media the tumor was mechanically dissociated for approximately 1 minute. The solution was then incubated for 30 minutes at 37° C. in 5% $CO_2$ and was then mechanically disrupted again approximately 1 minute. After being incubated again for 30 minutes at 37° C. in 5% $CO_2$, the tumor was mechanically disrupted a third time for approximately one minute. If after the third mechanical disruption, large pieces of tissue were present, one or two additional mechanical dissociations were applied to the sample, with or without 30 additional minutes of incubation at 37° C. in 5% $CO_2$. At the end of the final incubation, if the cell suspension contained a large number of red blood cells or dead cells, a density gradient separation using FICOLL branched hydrophilic polysaccharide (GE Healthcare, Smyrna, Ga.) was preformed to remove these cells.

TIL growth from digests and fragments were initiated in either gas permeable flasks with a 40 mL volume and a 10 $cm^2$ gas-permeable silicon bottom (G-Rex10, Wilson Wolf Manufacturing, New Brighton, Minn., USA) or 24-well plates (Corning Corning, N.Y.). When TIL cultures were initiated in 24-well plates (COSTAR 24-well cell culture cluster, flat bottom, Corning Incorporated, Corning, N.Y.), each well was seeded with $1 \times 10^6$ tumor digest cells or one tumor fragment approximately 1 to 8 $mm^3$ in size in 2 mL of CM with IL-2 (6000 IU/mL, Chiron Corp., Emeryville, Calif.). CM included RPMI 1640 with glutamine, supplemented with 10% AB serum, 25 mM Hepes and 10 µg/ml gentamicin. When cultures were initiated in G-Rex10 flasks, each flask was loaded with 10 to $40 \times 10^6$ viable tumor digest cells or 5 to 30 tumor fragments in 10 to 40 ml of CM with IL-2. Both the G-Rex10 and 24-well plates were incubated in a humidified incubator at 37° C. in 5% $CO_2$ and five days after culture initiation, half the media was removed and replaced with fresh CM and IL-2 and after day 5, half the media was changed every 2 to 3 days.

TIL Rapid Expansion Protocol (REP)

REP of TIL was performed using T-175 flasks and gas permeable bags as previously described (Tran et al., *J. Immunother.* 31(8):742-51 (2008); Dudley et al., *J. Immunother.* 26(4):332-42 (2003)) or gas permeable cultureware (G-Rex flasks). For TIL REP in T-175 flasks, $1 \times 10^6$ TIL suspended in 150 ml of media was added to each T-175 flask. The TIL were cultured with irradiated (50 Gy) allogeneic peripheral blood mononuclear cells (PBMC) as "feeder" cells at a ratio of 1 TIL to 100 feeder cells and the cells were cultured in a 1 to 1 mixture of CM and AIM-V medium, supplemented with 3000 IU per mL of IL-2 and 30 ng per ml of anti-CD3. The T-175 flasks were incubated at 37° C. in 5% $CO_2$. Half the media was exchanged on day 5 using 50/50 medium with 3000 IU per mL of IL-2. On day 7 cells from two T-175 flasks were combined in a 3 liter bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

For TIL REP in 500 mL capacity gas permeable flasks with 100 $cm^2$ gas-permeable silicon bottoms (G-Rex100, commercially available from Wilson Wolf Manufacturing Corporation, New Brighton, Minn., USA), $5 \times 10^6$ or $10 \times 10^6$ TIL were cultured with irradiated allogeneic PBMC at a ratio of 1 to 100 in 400 mL of 50/50 medium, supplemented with 5% human AB serum, 3000 IU per mL of IL-2 and 30 ng per ml of anti-CD3. The G-Rex100 flasks were incubated at 37° C. in 5% $CO_2$. On day 5, 250 mL of supernatant was removed and placed into centrifuge bottles and centrifuged at 1500 rpm (491×g) for 10 minutes. The TIL pellets were re-suspended with 150 mL of fresh medium with 5% human AB serum, 3000 IU per mL of IL-2, and added back to the original G-Rex100 flasks. When TIL were expanded serially in G-Rex100 flasks, on day 7 the TIL in each G-Rex100 were suspended in the 300 mL of media present in each flask and the cell suspension was divided into 3 100 mL aliquots that were used to seed 3 G-Rex100 flasks. Then 150 mL of AIM-V with 5% human AB serum and 3000 IU per mL of IL-2 was added to each flask. The G-Rex100 flasks were incubated at 37° C. in 5% $CO_2$ and after 4 days 150 mL of AIM-V with 3000 IU per mL of IL-2 was added to each G-Rex100 flask. The cells were harvested on day 14 of culture.

Cell Counts, Viability, Flow Cytometery

The expression of CD3, CD4, CD8 and CD56 was measured by flow cytometry with antibodies from BD Biosciences (BD Biosciences, San Jose, Calif.) using a FACSCanto™ flow cytometer (BD Biosciences). The cells were counted manually using a disposable hemacytometer and viability was assessed using trypan blue staining.

Cyokine Release Assays

TIL were evaluated for interferon-gamma (IFN-γ) secretion in response to stimulation either with OKT3 antibody or co-culture with autologous tumor digest. For OKT3 stimulation, TIL were washed extensively, and duplicate wells were prepared with $1 \times 10^5$ cells in 0.2 ml CM in 96 well flat-bottom plates pre-coated with 0.1 or 1.0 µg/mL of OKT-3 antibody diluted in PBS. After overnight incubation, the supernatants were harvested and IFN-γ in the supernatant was measured by ELISA (Pierce/Endogen, Woburn, Mass.). For the co-culture assay, TIL cells were placed into a 96-well plate with autologous tumor cells. After a 24 hour incubation, supernatants were harvested and IFN-γ release was quantified by ELISA.

Statistical Analysis

Values are mean one±standard error of the mean (SEM) unless otherwise indicated. Groups were compared using paired T tests.

Example 1

This example demonstrates that TIL cultured in gas-permeable containers is better than, or at least comparable to, that in a 24-well plate.

The growth of TIL from tumors using gas permeable flasks with a 40 mL capacity and 10 $cm^2$ gas permeable silicone bottom (G-Rex10, Wilson Wolf Manufacturing Corporation, New Brighton, Minn., USA (providing about 10 $cm^2$ of surface area for growth of the TIL)) or 24-well plates (Corning Corning, N.Y.) was compared. A total of 14 melanoma samples were tested, including 9 freshly prepared tumor digests (Table 1A) and 5 thawed samples from previously frozen tumor digests (Table 1B). TIL from frozen tumor from patient 2653 were not able to be cultured in either the G-Rex10 or 24-well plates. Except for one fresh sample (#3522), the ratio of harvested TIL to initially seeded cells at day 17 to 29 was similar to or better in the G-Rex10 flasks than in the 24-well plate (Table 1A and 1B).

TABLE 1A

Comparison of initial TIL culture in G-Rex10 flasks with 24-well plates using fresh tumor digests

| Sample Type | Patient # | Ratio of # TIL harvested/ # cell seeded | | TIL Viability (%) | | TIL Phenotype (% expressing CD3+CD8+) | |
|---|---|---|---|---|---|---|---|
| | | 24-well plate | G-Rex10 | 24-well plate | G-Rex10 | 24-well plate | G-Rex10 |
| Fresh Tumor Digest | 3520 | 1.28 | 1.17 | 92.80 | 93.30 | 26.50 | 31.60 |
| | 3522 | 2.14 | 1.46 | 92.10 | 95.10 | 39.80 | 48.70 |
| | 3523 | 2.34 | 2.30 | 94.50 | 93.60 | 15.00 | 37.60 |
| | 3524 | 1.27 | 6.22 | 80.20 | 95.00 | 76.70 | 86.60 |
| | 3546 | 5.86 | 7.60 | 90.40 | 93.80 | 44.60 | 37.30 |
| | 3552 | 3.20 | 5.83 | 94.90 | 97.10 | 43.10 | 72.40 |
| | 3556 | 3.60 | 4.15 | 96.20 | 96.20 | 35.40 | 31.20 |
| | 3560 | 6.06 | 6.25 | 95.80 | 97.20 | 32.30 | 38.60 |
| | 3561 | 4.76 | 6.38 | 94.70 | 93.90 | 65.80 | 83.40 |
| Average ± SEM | | 3.39 ± 0.61 | 4.60 ± 0.80 | 92.40 ± 1.65 | 95.02 ± 0.50 | 42.13 ± 6.33 | 51.93 ± 7.51 |

TABLE 1B

Comparison of initial TIL culture in G-Rex10 flasks with 24-well plates using frozen tumor digests

| Sample Type | Patient # | Ratio of # TIL harvested/ # cell seeded | | TIL Viability (%) | | TIL Phenotype (% expressing CD3+CD8+) | |
|---|---|---|---|---|---|---|---|
| | | 24-well plate | G-Rex10 | 24-well plate | G-Rex10 | 24-well plate | G-Rex10 |
| Frozen Tumor Digest | 2653 | 0.16 | 0.19 | 87.70 | 90.60 | N.T. | N.T. |
| | 3289 | 2.43 | 5.30 | 95.10 | 98.00 | 70.40 | 73.60 |
| | 2976 | 7.26 | 7.50 | 99.00 | 99.00 | 66.30 | 70.00 |
| | 3071 | 1.79 | 6.05 | 88.40 | 97.70 | 37.50 | 29.10 |
| | 2998 | 3.36 | 5.00 | 96.30 | 97.00 | 64.40 | 75.80 |
| Average ± SEM | | 3.00 ± 1.18 | 4.81 ± 1.23 | 93.30 ± 2.24 | 96.46 ± 1.50 | 59.65 ± 6.70 | 62.12 ± 9.91 |

N.T. = Not tested.

The viability and percentage of cells expressing CD3 and CD8 between these two types of vessels were similar (Tables 1A and 1B). TIL were obtained from 13 of the 14 samples. These results suggest that TIL growth in G-Rex10 is better than, or at least comparable to, that in a 24-well plate.

IFN-γ production by TIL cultured in G-Rex10 flasks was also compared with that of TIL cultured in 24-well plates. IFN-γ production following stimulation with autologous tumor by TIL from 4 patients cultured in both types of vessels was similar (Table 1C)

TABLE 1C

Interferon-γ release (pg/ml) by unstimulated and tumor-stimulated TIL

| | | Tumor Target[1] | | |
|---|---|---|---|---|
| Patient | Growth Method | None | Allogeneic | Autologous |
| 3552 | plate | 114 | 157 | >1541 |
| | G-Rex10 | 81 | 338 | >1577 |
| 3556 | plate | 90 | 184 | 139 |
| | G-Rex10 | 87 | 363 | 282 |
| 3560 | plate | 135 | 175 | 318 |
| | G-Rex10 | 104 | 212 | 572 |
| 3561 | plate | 70 | 97 | 207 |
| | G-Rex10 | 84 | 128 | 253 |

[1]Cryopreserved enzymatically digested single cell tumor suspension was thawed and 1 × 10$^5$ viable tumor cells were cocultured with TIL (1:1 ratio) overnight before quantifying interferon-γ in the supernatant by ELISA. Values in bold are more than two times background and >200 pg/ml.

Example 2

This example demonstrates that the culture of TIL from tumor fragments in gas permeable flasks produces a greater number of TIL as compared to culture in 24-well plates after 7 to 13 days.

The growth of TIL from tumor fragments in G-Rex10 flasks or 24-well plates was next compared. For each tumor sample, fragments approximately 1 to 8 mm$^3$ in size were seeded into 24-well plates at 1 piece per well and into G-Rex10 flasks at 5, 10, 20, or 30 pieces per flask. The growth of TIL from 2 lymph nodes and 1 liver metastasis was assessed (Table 2). TIL could be grown from tumor fragments in both gas-permeable flasks and 24-well plates, but after 7 to 13 days greater quantities of TIL were obtained from the G-Rex10 flasks than the wells (Table 2).

TABLE 2

Initial TIL culture using tumor fragments in G-Rex10 flasks and 24-well plates.

| Patient Number and Tumor Source | Culture Vessel | Tumor Fragments* | Number of Cells TIL# (Day 7-13) | # of TIL per fragment | TIL Viability (%) | TIL Phenotype (% TIL expressing each antigen) CD3+ | CD3+CD4+ | CD3+CD8+ | CD56+ |
|---|---|---|---|---|---|---|---|---|---|
| 3581 (Lymphnode) | Wells | 1 per well, 5 total | $2.71 \times 10^7$ | $5.42 \times 10^6$ | 93.2% | 53.4% | 40.2% | 10.3% | 11.6% |
| | G-Rex10 | 5 fragments | $4.29 \times 10^7$ | $8.58 \times 10^6$ | 97.0% | 61.0% | 44.0% | 14.3% | 7.9% |
| | G-Rex10 | 10 fragments | $8.02 \times 10^7$ | $8.02 \times 10^6$ | 95.4% | 58.5% | 42.2% | 13.7% | 9.3% |
| | G-Rex10 | Dissociated tumor | $4.82 \times 10^7$ | $2.41 \times 10^6$ | 96.4% | 60.3% | 40.1% | 16.3% | 8.9% |
| 3584 (Liver) | Wells | 1 per well, 5 total | $1.52 \times 10^7$ | $3.04 \times 10^6$ | 92.7% | 89.2% | 19.8% | 68.8% | 5.3% |
| | G-Rex10 | 5 fragments | $4.38 \times 10^7$ | $8.76 \times 10^6$ | 95.7% | 92.0% | 10.6% | 81.1% | 2.1% |
| | G-Rex10 | 10 fragments | $8.13 \times 10^8$ | $8.13 \times 10^6$ | 94.4% | 91.4% | 9.8% | 81.2% | 2.3% |
| | G-Rex10 | Dissociated tumor | $4.94 \times 10^7$ | $2.60 \times 10^6$ | 95.8% | 87.7% | 11.7% | 75.6% | 3.3% |
| 3585 (Lymphnode) | Wells | 1 per well, 5 total | $2.34 \times 10^7$ | $4.68 \times 10^6$ | 95.8% | 85.5% | 14.4% | 68.6% | 4.20% |
| | G-Rex10 | 5 fragments | $6.41 \times 10^7$ | $12.8 \times 10^6$ | 95.0% | 92.1% | 20.6% | 70.7% | 1.10% |
| | G-Rex10 | 10 fragments | $1.12 \times 10^8$ | $11.2 \times 10^6$ | 97.2% | 93.4% | 18.6% | 73.9% | 1.30% |
| | G-Rex10 | Dissociated tumor | $3.33 \times 10^7$ | $1.23 \times 10^6$ | 90.0% | 90.4% | 24.0% | 65.7% | 2.60% |

*Each tumor fragment was approximately 1 mm$^3$.

Figure 1A:
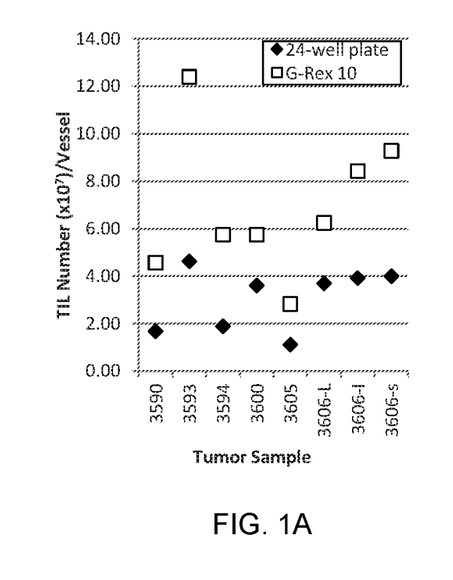
FIG. 1A is a graph showing the numbers of TIL produced by 10 tumor fragments from eight tumor samples in 24-well plates (diamonds) and G-Rex10 flasks (squares). For each individual tumor sample, 10 fragments were seeded into a 24-well plate at 1 piece per well and 10 fragments were seeded into a single G-Rex10 flask. Cells were harvested by 7 to 23 days of culture, pooled if collected from 24-well plate, and counted. A total of 8 samples were tested.
Figure 1B:
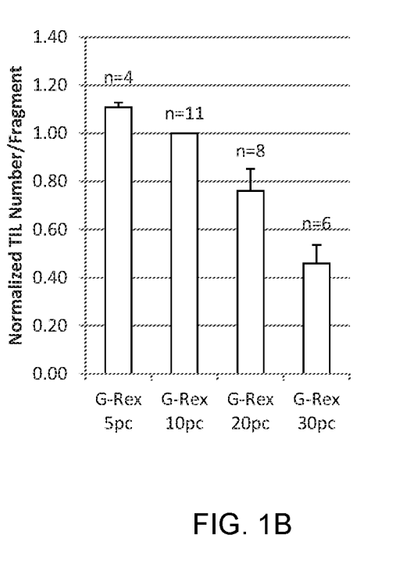
FIG. 1B is a graph showing the number of TIL produced per each tumor fragment by 7 to 23 days of culture of 5, 10, 20 and 30 tumor fragments in G-Rex10 flasks. Because only G-Rex10 flasks with 10 fragments were used in all experiments, the data were normalized using the number of cells produced in G-Rex10 flasks with 10 fragments. The number of TIL produced in each flask was divided by the number of fragments in the flask and this value was divided by the number of TIL produced in G-Rex10 flasks with 10 fragments from the same patient divided by 10. The average number of TIL produced by each tumor fragment in G-Rex10 flasks seeded with 10 fragments was $7.51 \times 10^6$ cells per fragment (n=11).
Figure 1C:
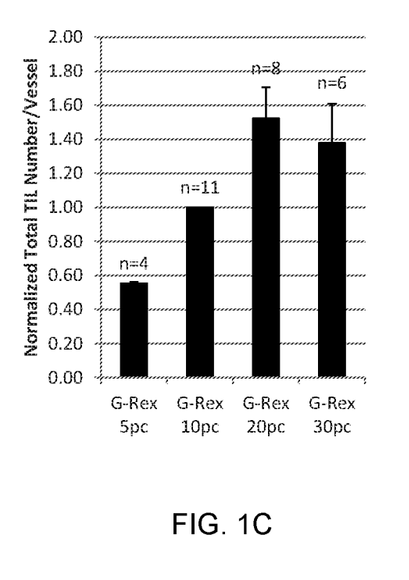
FIG. 1C is a graph showing the total number of TIL produced by 7 to 23 days of culture of 5, 10, 20 and 30 tumor fragments in G-Rex10 flasks. The data were normalized using the number of cells produced in G-Rex10 flasks with 10 fragments. The total number TIL produced in each G-Rex10 flask was divided by the number of TIL produced by each G-Rex10 flask seeded with 10 tumor fragments from the same patient. The average number of TIL produced by G-Rex10 flasks seeded with 10 tumor fragments was $75.1 \times 10^6$ (n=11).

A total of 11 tumor samples collected from 9 patients were tested; 3 samples were from 1 patient, but they were from different metastatic tumors. TIL could be grown from tumor fragments from all 11 samples in both the G-Rex10 flasks and 24-well plates, but after 7 to 23 days in culture greater quantities of TIL were obtained from the G-Rex10 flasks. The head-to-head comparison of culturing 10 fragments in the two types of vessels showed that TIL yields from G-Rex10 flasks were consistently higher than those from 24-well plate (FIG. 1A). The optimal numbers of fragments seeded into each G-Rex10 flasks was further assessed. The quantities of TIL obtained per tumor fragment decreased as the number of pieces added to each G-Rex10 flask increased (FIG. 1B), however, total TIL yield was higher as more fragments were cultured in the G-Rex10 flasks until 20 or more tumor fragments were cultured in each G-Rex10 flask (FIG. 1C). The viability of TIL obtained from G-Rex10 flasks was similar to that of TIL obtained from 24-well plates (96.6±0.6% vs 95.3±0.8%) as was the proportion of TIL expressing CD3 and CD8 (67.8±7.2% vs 63.3±7.7%). TIL were also obtained from 3 of the 11 samples by the culture of mechanically dissociated samples in G-Rex10 flasks, but greater yields were obtained using tumor fragments as the starting material.

Example 3

This example demonstrates the kinetics of TIL growth in gas-permeable flasks.

In order to assess the kinetics of TIL growth in gas-permeable cultureware, TIL from one patient were cultured in G-Rex100 flasks seeded at a density of $5 \times 10^6$ and $10 \times 10^6$ cells per flask. The cells were counted daily after day 6. On Day 6 the number of cells in the G-Rex100 flask seeded at $5 \times 10^6$ cells was $255 \times 10^6$ cells and at $10 \times 10^6$ cells was $300 \times 10^6$ cells. The quantity of TIL in G-Rex100 flasks seeded at each cell density increased steadily until day 9, but there was little increase in cell counts between days 9 and 10. After 10 days $906 \times 10^6$ cells were harvested from flasks seeded with $5 \times 10^6$ TIL and $1,050 \times 10^6$ cells from flasks seeded with $10 \times 10^6$ TIL. Although TIL expanded well for 9 days, in order to keep the G-Rex100 flask expansion process similar to REP in T-flasks and gas-permeable bags where TIL are transferred from T-flasks to bags on day 7, further studies focused on TIL expansion in the G-Rex100 flasks for 7 days.

Example 4

This example demonstrates that a 7-day culture of TIL in a gas permeable container seeded with $10 \times 10^6$ cells does not produce a significantly greater number of cells than a gas permeable container seeded with $5 \times 10^6$ cells.

The first step in TIL rapid expansion protocol (REP) has traditionally been performed in T-175 flasks. The expansion of TIL in T-175 flasks was compared to expansion in G-Rex100 flasks (providing about 100 cm$^2$ of surface area for growth of the TIL). The expansion of TIL from 4 patients over 7 days in G-Rex100 flasks seeded with $5 \times 10^6$ and $10 \times 10^6$ cells was compared with TIL expansion in T-175 flasks (Table 3). T-175 flasks were seeded with $1 \times 10^6$ cells.

TABLE 3

Comparison of TIL rapid expansion process (REP) over 7 days in T-175 flasks* and G-Rex100 flasks seeded with $5 \times 10^6$ or $10 \times 10^6$ TIL.

| | Fold Increase | | | Viability (%) | | | Phenotype (% CD3+CD8+) | | |
|---|---|---|---|---|---|---|---|---|---|
| Patient | T-175 | G-Rex100 $5 \times 10^6$ | G-Rex100 $10 \times 10^6$ | T-175 | G-Rex100 $5 \times 10^6$ | G-Rex100 $10 \times 10^6$ | T-175 | G-Rex100 $5 \times 10^6$ | G-Rex100 $10 \times 10^6$ |
| 2812 | 74 | 88 | 57 | 95.8 | 96.6 | 94.7 | 66.4 | 64.6 | 60.5 |
| 3289 | 183 | 218 | 139 | 96.4 | 94.8 | 95.1 | 79.7 | 83.7 | 84.1 |
| 2976 | 254 | 250 | ND | 94.1 | 96.1 | ND | 55.2 | 59.9 | ND |
| 3071 | 156 | 146 | ND | 87.4 | 90.3 | ND | 44.6 | 41.6 | ND |
| Mean | 167 ± 74 | 176 ± 73 | 98 ± 58 | 93.5 ± 2.9 | 94.5 ± 2.9 | 94.9 ± 0.3 | 61.5 ± 15.0 | 62.5 ± 17.3 | 72.3 ± 16.7 |

*T-175 flasks were seeded with $1 \times 10^6$ TIL.

After 7 days of culture of TIL from 4 patients, the number of cells in T-175 flasks increased to $206\pm103\times10^6$ cells which represented an expansion of $167\pm74$ fold (Table 3). The culture of TIL from the same 4 patients in G-Rex100 flask seeded with $5\times10^6$ cells resulted in the production of $877\pm365\times10^6$ cells which represented an expansion of $176\pm73$ fold. The culture of TIL from 2 of the 4 patients in G-Rex100 flask seeded with $10\times10^6$ cells resulted in the production of $980\pm580\times10^6$ cells which represented an expansion of $98\pm58$ fold. The viability and proportion of cells that expressed CD3 and CD8 were similar among those produced by the three different conditions (Table 3). These results suggest that the performance of G-Rex100 flasks seeded at the lower seeding density was comparable to that of the T-175 flasks. Since the 7-day culture of TIL in G-Rex100 flasks seeded with $10\times10^6$ cells did not produce a significantly greater number of cells than the G-Rex100 flask seeded with $5\times10^6$ cells, the lower seeding density was chosen for future experiments.

Example 5

This example demonstrates that a similar number of cells can be produced in a 500 mL gas permeable container as compared to a 2000 mL gas permeable container.

Since the maximum cell yield from one G-Rex100 flask reached a plateau after approximately 9 days, the production of adequate quantities of TIL for clinical therapy requires the splitting of cells during REP and transferring the cells into multiple gas-permeable flasks for further culture. TIL REP by serial culture was tested in G-Rex100L, another type of gas-permeable flask that is commercially available for large scale cell expansion (Wilson Wolf Manufacturing Corporation, New Brighton, Minn., USA). The G-Rex100L has the same gas permeable surface area on the silicone bottom of the flask as the G-Rex100 (providing about 100 cm² of surface area for growth of the TIL), but the G-Rex100L is taller. As a result, the media capacity of the G-Rex100 L flask is approximately 2000 ml compared to approximately 500 mL for the G-Rex100.

TIL expansion was compared in these two types of flasks. TIL were initially seeded at a density of $5\times10^6$ cells for both the G-Rex100 and G-Rex100L flasks, and were cultured for 7 days as described in Example 3. After 7 days the cells from the G-Rex100 flask were split into 3 equal parts, and seeded into 3 G-Rex100L flasks. The cells from the G-Rex100 L flask were split into two equal parts, seeded into 2 G-Rex100L flasks. The TIL were cultured for an additional 7 days in the G-Rex100 and G-Rex100L flasks.

The expansion of TIL from two patients was compared in the G-Rex100 and G-Rex100L flasks. Both patients' TIL growth slowed after 13 or 14 days. The total number of cells produced after 14 days by culture in the 3 G-Rex100 flasks and the 2 G-Rex100L flasks was similar for one patient (about $9\times10^9$ cells in G-Rex100 and G-Rex100L after 14 days) but was greater in the G-Rex100 flask for the second (about $12\times10^9$ cells in G-Rex100 and $8.4\times10^9$ cells in G-Rex100L after 14 days)). Since a similar volume of media is required to produce a similar number of cells in the G-Rex100 and in the G-Rex100L flasks and since the G-Rex100 flasks are easier to handle, initial expansion of TIL in one G-Rex100 flask followed by expansion in 3 G-Rex100 flasks was chosen for future experiments.

Example 6

This example demonstrates the consistency of serial TIL expansion using gas permeable containers and a "full scale" expansion of TIL using gas permeable containers.

The consistency of serial TIL expansion in G-Rex100 flasks using cells from 14 patients was tested. Initially, $5\times10^6$ TIL were seeded into a G-Rex100 flask and the cells were cultured for 7 days. They were then split into 3 equal parts, seeded into 3 G-Rex100 flasks. After 14 days in culture, $8.60\times10^9\pm2.80\times10^9$ TIL with a range of $2.24\times10^9$ to $12.8\times10^9$ were produced. The number of TIL produced after 14 days was similar for 12 patients, but lower for two others. When the 2 patients with the lowest overall TIL expansion were excluded, the mean quantity of TIL produced was $9.55\times10^9$ cells per original G-Rex100 flask. The mean cell concentration in G-Rex100 flasks at the end of the culture was $7.95\times10^6$ cells per mL.

The IFN-γ release from TIL produced by G-Rex100 REP and T-175 flask/bag REP was compared. TIL samples produced by both REP methods using the same tumor samples from 4 patients were tested. Following stimulation by anti-CD3 IFN-γ production by TIL expanded in G-Rex100 flasks was similar to that of TIL expanded in T-175 flasks and bags (Table 4A).

TABLE 4A

| | | IFN-γ release (pg/ml)[2] | | |
|---|---|---|---|---|
| Patient[1] | Sample | OKT3 1.0 µg/ml | OKT3 1.0 µg/ml | None |
| 3536 | Flask/Bag | 631, 672 | 457, 390 | 0, 0 |
| | G-Rex100 | 579, 553 | 243, 277 | 0, 0 |
| 3539 | Flask/Bag | 12272, 14350 | 10553, 11039 | 179, 176 |
| | G-Rex100 | 29792, 29550 | 26670, 23835 | 73, 80 |
| 3135 | Flask/Bag | 831, 1124 | 704, 643 | 0, 0 |
| | G-Rex100 | 581, 635 | 151, 74 | 2, 1 |
| 3533 | Flask/Bag | 6870, 6370 | 4280, 500 | 114, 146 |
| | G-Rex100 | 5100, 4510 | 1513, 1407 | 136, 150 |

[1]TIL cells were stimulated by overnight incubation on plate bound OKT3 (anti-CD3 antibody) coated at the concentration indicated.
[2]Values are IFN-γ (pg/ml) detected in duplicate wells measured by ELISA.

These results suggested that 20 to $30\times10^9$ TIL could be produced by the initial culture of $15\times10^6$ TIL in 3 G-Rex100 flasks for 7 days followed by a second 7 day culture in 9 G-Rex100 flasks (Table 4B).

TABLE 4B

|  | Day 0 Seeding | Day 5 Medium Change | Day 7 Split (1:3) | Day 11 Media Addition | Day 14 Harvest/Wash |
|---|---|---|---|---|---|
| Containers | 3 G-Rex100 | 3 G-Rex100 | 9 G-Rex100 | 9 G-Rex100 |  |
| Final Volume of Medium | 400 mL/container | 300 mL | 250 mL | 400 mL |  |
| Steps | $5 \times 10^6$ cells TIL are seeded in 400 mL in each of 3 G-Rex100 flasks | Remove 250 mL of media; spin down and resuspend TIL in 150 mL and add to remaining 150 mL | 300 mL for each G-Rex100 is split into 3 100 mL aliquots; 100 mL added to 3 G-Rex100 flasks; an additional 150 mL of media is added | 250 mL in each flask and 150 mL new media | TIL are harvested, pooled and washed |

To test this "full scale" G-Rex100 REP, $15 \times 10^6$ TIL from one patient were divided among three G-Rex100 flasks, A, B and C. After 7 days in culture the TIL in each flask were split into 3 equal parts, seeded into 3 G-Rex100 flasks and cultured for an additional 7 days. The mean number of TIL harvested from each of the 3 G-Rex100 flasks used for initial expansion was $875 \times 10^6 \pm 30.8 \times 10^6$ and ranged from $849 \times 10^6$ to $909 \times 10^6$ TIL and the mean number harvested from each of the 9 G-Rex100 flasks used for the secondary expansion was $2.63 \pm 0.09 \times 10^9$ and ranged for $2.55 \times 10^9$ to $2.70 \times 10^9$ TIL (Table 5).

While serial expansion of TIL in G-Rex100 flasks required far less regents, less incubator space, less labor and less specialized equipment than REP in T-flasks and gas-permeable bags, it was hypothesized that the gas-permeable cultureware REP process could be further improved by using one large vessel rather than 9 G-Rex100 flasks. Therefore, a larger vessel with a gas-permeable membrane with approximately 6.5 times the gas permeable surface area and 10 times the volume of the G-Rex100 flasks was tested. This vessel was the GP5000 (providing about 650 cm$^2$ of surface area for growth of the TIL). Two different REP methods

TABLE 5

Number of cells produced by a two-step G-Rex100 TIL rapid expansion protocol (REP); the first step involved growth in 3 G-Rex100 flasks and the second growth in 9 G-Rex100 flasks

| First G-Rex100 Flask | Day 0 | Day 7 | Second G-Rex100 Flask | Day 11 | Day 14 | Post Wash |
|---|---|---|---|---|---|---|
| A | $5 \times 10^6$ | $849 \times 10^6$ | A1 | $1.44 \times 10^9$ | $2.67 \times 10^9$ |  |
|  |  |  | A2 | N.T. | $2.43 \times 10^9$ |  |
|  |  |  | A3 | N.T. | $2.66 \times 10^9$ |  |
| B | $5 \times 10^6$ | $867 \times 10^6$ | B1 | $1.55 \times 10^9$ | $2.70 \times 10^9$ |  |
|  |  |  | B2 | N.T. | $2.66 \times 10^9$ |  |
|  |  |  | B3 | N.T. | $2.76 \times 10^9$ |  |
| C | $5 \times 10^6$ | $909 \times 10^6$ | C1 | $1.44 \times 10^9$ | $2.62 \times 10^9$ |  |
|  |  |  | C2 | N.T. | $2.60 \times 10^9$ |  |
|  |  |  | C3 | N.T. | $2.55 \times 10^9$ |  |
| Total | $15 \times 10^6$ | $2.63 \times 10^9$ |  | $14 \times 10^9$ | $23.6 \times 10^9$ | $21.0 \times 10^9$ |

The total TIL yield was $23.6 \times 10^9$ and $21.0 \times 10^9$ remained after washing the cells. The viability of the cells was 96% and 69% of the cells expressed CD3 and CD8.

Cell potency, in terms of interferon (IFN)-γ secretion was also tested using Enzyme-linked immunosorbent assay (ELISA). The cells grown using the gas-permeable G-Rex100 containers and the cells grown using non-gas permeable containers produced a comparable amount of IFN-γ.

Example 7

This example demonstrates the rapid expansion of TIL using one 5000 mL gas permeable container.

using GP5000 gas-permeable vessels were tested. One method involved an initial 7-day expansion in 2 G-Rex100 flasks, each seeded with $5 \times 10^6$ TIL, followed by another expansion of the harvested TIL in a single GP5000 vessel. The other method involved a single 14-day expansion of $10 \times 10^6$ TIL in a GP5000 vessel.

Cells from 2 patients were tested and the TIL yield of the two REP methods were similar for both donors. Approximately $25 \times 10^9$ TIL were harvested from patient 3524 and approximately $20 \times 10^9$ from patient 3560. The cell viability for all four REPs was >96% and >92% of patient 3524 cells expressed CD8 and >35% of patient 3560 cells expressed CD8.

Example 8

This example demonstrates a clinical TIL production process.

Clinical scale TIL production using tumor fragments from 3 patients was next tested by initially culturing TIL in G-Rex10 flasks followed by REP in G-Rex100 flasks. For each patient, 6 G-Rex10 flasks were seeded with 5 tumor fragments and after 14 to 15 days $5\times10^6$ TIL from each G-Rex10 flask were seeded into one G-Rex100 flask. After 7 days TIL from each G-Rex100 flask were split into 3 G-Rex100 flasks and after an additional 7 days in culture TIL were harvested from the 18 G-Rex100 flasks. For two patients, 3613 and 3618, enough TIL could be harvested from each of the 6 G-Rex10 flasks for TIL REP in a G-Rex100 flask.

The quantity of TIL harvested from each of the G-Rex10 flasks ranged from 47.5 to $97.8\times10^6$ cells for patient 3613 and 24.6 to $64.2\times10^6$ for patient 3618 (Table 6A). For patient 3625 sufficient quantities of TIL were obtained from 4 of the 6 G-Rex10 flasks. The quantity harvested from these 4 flasks ranged from 59.7 to $140\times10^6$ cells (Table 6A). For patients 3613 and 3618, $5\times10^6$ TIL from each of the 6 G-Rex10 flasks was seeded into a G-Rex100 flask. For patient 3625, $5\times10^6$ TIL from 2 G-Rex10 flasks were each seeded into one G-Rex100 flask and $10\times10^6$ TIL from the other 2 G-Rex10 flasks were split and used to seed 4 G-Rex100 each with $5\times10^6$ TIL. At the completion of REP using patient 3613 cells $22.4\times10^9$ TIL were harvested, while REP using patient 3618 cells yielded $52.7\times10^9$ TIL and patient 3625 cells yielded $61.0\times10^9$ TIL. The number of TIL produced by each of the 6 sets of 3 G-Rex100 flasks was similar for each patient. These results show that G-Rex100 flasks can produce sufficient quantities of TIL for clinical therapy using TIL initially cultured from tumor fragments in G-Rex10 flasks. The same G-Rex100 REP protocol was also successful in expanding TIL that were initially cultured from tumor fragments in 24-well plates. There were no significant differences in fold expansion using either TIL initially cultured from tumor fragments in 24-well plates or G-Rex10 flasks.

TABLE 6A

| Patient # | Culture Vessel | # of Fragments Seeded | Day TIL Harvested | # TIL Harvested | #TIL/Fragment | Viability (%) | TIL Phenotype (% CD3+ CD8+) |
|---|---|---|---|---|---|---|---|
| 3613 | 1 | 5 | 14 | $47.5 \times 10^6$ | $9.50 \times 10^6$ | N.T. | 70 |
|  | 2 | 5 | 14 | $94.5 \times 10^6$ | $18.9 \times 10^6$ | N.T. | 74 |
|  | 3 | 5 | 14 | $57.5 \times 10^6$ | $11.5 \times 10^6$ | N.T. | 74 |
|  | 4 | 5 | 14 | $97.8 \times 10^6$ | $19.6 \times 10^6$ | N.T. | 73 |
|  | 5 | 5 | 14 | $55.0 \times 10^6$ | $11.0 \times 10^6$ | N.T. | 67 |
|  | 6 | 5 | 14 | $67.0 \times 10^6$ | $13.4 \times 10^6$ | N.T. | 67 |
| 3618 | 1 | 5 | 14 | $61.0 \times 10^6$ | $12.2 \times 10^6$ | 99.0 | 77 |
|  | 2 | 5 | 14 | $64.2 \times 10^6$ | $12.8 \times 10^7$ | 97.0 | 84 |
|  | 3 | 5 | 14 | $24.6 \times 10^6$ | $4.92 \times 10^6$ | 99.2 | N.T. |
|  | 4 | 5 | 14 | $64.2 \times 10^6$ | $12.8 \times 10^6$ | 96.4 | 86 |
|  | 5 | 5 | 14 | $40.2 \times 10^6$ | $8.04 \times 10^6$ | 97.1 | 77 |
|  | 6 | 5 | 14 | $57.0 \times 10^6$ | $11.4 \times 10^6$ | 99.3 | 85 |
| 3625 | 1 | 5 | 15 | $86.0 \times 10^6$ | $17.2 \times 10^6$ | 96.8 | 73 |
|  | 2 | 5 | 15 | $59.4 \times 10^6$ | $11.9 \times 10^6$ | 98.7 | 91 |
|  | 3 | 5 | 15 | $71.8 \times 10^6$ | $14.4 \times 10^6$ | 98.6 | 73 |
|  | 4 | 5 | 15 | $1.80 \times 10^{6}$** | $0.36 \times 10^6$ | 64.3 | N.T. |
|  | 5 | 5 | 15 | $2.20 \times 10^{6}$** | $0.440 \times 10^6$ | 78.6 | N.T. |
|  | 6 | 5 | 15 | $140 \times 10^6$ | $28.0 \times 10^6$ | 100.0 | 74 |

N.T. = Not Tested
**Insufficient number of cells for clinical REP

Example 9

This example demonstrates that expanding TIL in gas permeable containers uses a lower number of containers, lower number of feeder cells, and lower amount of medium as compared to methods in which the TIL are expanded in non-gas permeable containers.

TIL are expanded as described above using gas permeable containers (G-Rex100 and GP5000) and in non-gas permeable containers (bags and T 175 flask). A comparison of the numbers of containers and amounts reagents used is set forth in Table 6B.

TABLE 6B

|  | No. of Containers | No. of TIL seeded | No. of Feeder Cells | Volume of Medium |
|---|---|---|---|---|
| T 175 Flask | 20-40 Flasks | $20 \times 10^6$-$40 \times 10^6$ | $4 \times 10^9$-$8 \times 10^9$ | ~30,000 ml (requires 2 different types of REP medium) |

TABLE 6B-continued

| | No. of Containers | No. of TIL seeded | No. of Feeder Cells | Volume of Medium |
|---|---|---|---|---|
| LIFECELL flasks (Baxter) | 10-20 Bags | $20 \times 10^6$-$40 \times 10^6$ | $4 \times 10^9$-$8 \times 10^9$ | ~30,000 ml |
| 500 mL gas permeable container (G-Rex100) | 12-18 | $20 \times 10^6$-$30 \times 10^6$ | $2 \times 10^9$-$2 \times 10^9$ | 5800 ml-8700 ml (only 1 REP medium is necessary) |
| 5000 mL gas permeable container (GP5000) | 2 | $20 \times 10^6$-$30 \times 10^6$ | $2 \times 10^9$-$2 \times 10^9$ | 5800 ml-8700 ml (only 1 REP medium is necessary) |

Example 10

This example demonstrates that culturing TIL in unfiltered cell medium has little or no detrimental effects on TIL growth.

TIL ($4 \times 10^6$) were cultured in filtered or unfiltered complete medium (CM) (50 mL) (RPMI 1640 with glutamine, supplemented with 10% AB serum, 25 mM Hepes and 10 μg/ml gentamicin) in four wells. On day 7/8, fold increase, viability, and % CD3+CD8+ were measured. The results are shown in Table 7.

TABLE 7

| | Fold Increase | | Viability | | % CD3+CD8+ | |
|---|---|---|---|---|---|---|
| Group | #2812 | #3289 | #2812 | #3289 | #2812 | #3289 |
| Filtered Medium | 2.02 | 9.62 | 97% | 95.2% | 59% | 90% |
| Unfiltered Medium | 2.13 | 9.40 | 96.5% | 95.9% | 60.2% | 89% |

The performance of the TIL cultured in the non-filtered medium was similar to that of the TIL cultured in the filtered medium. The results suggest that particulate serum components have little or no detrimental effects on TIL cell growth.

Example 11

This example demonstrates that culturing TIL in cell medium that lacks beta-mercaptoethanol (BME) has little or no detrimental effects on TIL growth or potency.

TIL were cultured in complete medium (CM) (50 mL) with or without BME. After 2-3 weeks, population increase, viability, and % CD3+CD8+ were measured. The results are shown in Table 8. $\times 10^7$

TABLE 8

| Tumor # | Group | # of Cells Seeded | TIL# Harvest Day; D17-29) | Ratio | Viability (Harvest Day) | CD3CD8 (Harvest Day) |
|---|---|---|---|---|---|---|
| 3520 | +BME | $1.80 \times 10^7$ | $2.72 \times 10^7$ | 1.51 | 93.40% | 59.60% |
| | −BME | $1.80 \times 10^7$ | $2.11 \times 10^7$ | 1.17 | 93.30% | 31.60% |
| 3522 | +BME | $3.00 \times 10^7$ | $4.18 \times 10^7$ | 1.39 | 94.80% | 51.40% |
| | −BME | $3.00 \times 10^7$ | $4.39 \times 10^7$ | 1.46 | 95.10% | 48.70% |
| 3523 | +BME | $3.00 \times 10^7$ | $6.75 \times 10^7$ | 2.25 | 95.50% | 33.90% |
| | −BME | $3.00 \times 10^7$ | $6.90 \times 10^7$ | 2.30 | 93.60% | 37.60% |
| 3524 | +BME | $1.80 \times 10^7$ | $1.17 \times 10^8$ | 6.52 | 94.50% | 91.10% |
| | −BME | $1.80 \times 10^7$ | $1.12 \times 10^8$ | 6.23 | 95.00% | 86.50% |

The performance of the TIL cultured in the medium without BME was similar to that of the TIL cultured in the medium with BME.

Potency of the TIL is measured and compared for TIL cultured in medium with or without BME. Effector (TIL) cells ($1 \times 10^5$) are co-cultured with target (antigen-presenting tumor cells) cells ($1 \times 10^5$), with AK1700 used as a negative control and DM5 A2 used as a positive control. IFN-gamma secretion is measured by ELISA. There was no significant difference in IFN-gamma secretion for the TIL cultured in medium without BME as compared to TIL cultured in medium with BME. Thus, the absence of BME from the medium has little or no detrimental effects on TIL cell growth or potency.

Example 12

This example demonstrates that feeding the TIL no more frequently than every third or fourth day during expansion of the number of TIL in a gas permeable container has little or no detrimental effects on TIL growth.

TIL were rapidly expanded in a 500 mL gas permeable container (G-Rex100) as described above and fed as described in Table 9. At the end of 14 days, fold expansion, viability, and composition were measured.

TABLE 9

| | Original | Day 7 | Day 9 | Day 11 | Day 13 | Day 14 (total) |
|---|---|---|---|---|---|---|
| Standard (Fed every other day) | 100 ml | +100 ml | +50 ml | +100 ml | +50 ml | 400 ml |
| Modified (Fed every third or fourth Day) | 100 ml | +150 ml | — | +150 ml | — | 400 ml |

There was no difference in the fold expansion observed for TIL fed every third or fourth day as compared to TIL fed every other day. Viability and cell composition are set forth in Table 10.

TABLE 10

| Sample | Group | Viability (%) | Phenotyping (%) | | | |
|---|---|---|---|---|---|---|
| | | | CD3 | CD3CD4 | CD3CD8 | CD56 |
| #2761 | Standard | 98.1 | 98.4 | 40.4 | 49.3 | 0.6 |
| | Modified | 97.7 | 98.6 | 39.9 | 51.8 | 0.5 |
| #3522 | Standard | 98.9 | 96.8 | 29.9 | 59.9 | 1.6 |
| | Modified | 98.4 | 97.0 | 28.8 | 60.2 | 1.5 |
| #3523 | Standard | 96.1 | 98.3 | 20.0 | 72.3 | 0.2 |
| | Modified | 95.7 | 98.4 | 20.2 | 72.1 | 0.2 |
| #3524 | Standard | 92.7 | 99.1 | 1.5 | 95.5 | 0.1 |
| | Modified | 90.2 | 99.3 | 1.4 | 95.2 | 0.1 |

Potency of the TIL is measured and compared for TIL cultured and fed every third or fourth day as compared to TIL fed every other day. Effector cells ($1 \times 10^5$) are co-cultured with target cells ($1 \times 10^5$), with AK1700 used as a negative control and DM5 A2 used as a positive control. IFN-gamma secretion is measured by ELISA. There was no significant difference in IFN-gamma secretion for the TIL fed every third or fourth day as compared to TIL fed every other day. Thus, the reduction in feeding frequency has little or no detrimental effects on TIL potency.

There was no difference in viability or cell composition observed for TIL fed every third of fourth day as compared to TIL fed every other day.

Example 13

This example demonstrates that using no more than one type of cell culture medium for expanding the number of TIL has little or no detrimental effects on TIL growth.

TIL were rapidly expanded as described above using no more than one type of cell culture medium or two types of cell culture medium as set forth in Table 11.

TABLE 11

| | Day 0 | Day 5 | Day 7 | Day 11 |
|---|---|---|---|---|
| Standard (2 medium types) | 50% RPMI 50% AIM-V 5% Serum + Hepes + IL-2 + OKT3 | 50% RPMI 50% AIM-V 5% Serum + Hepes + IL-2 | 100% AIM-V 5% Serum + GlutaMAX + IL-2 | 100% AIM-V + GlutaMAX + IL-2 |
| Modified (No more than 1 medium type) | 100% AIM-V 5% Serum + GlutaMAX + IL-2 + OKT3 | 100% AIM-V 5% Serum + GlutaMAX + IL-2 | 100% AIM-V 5% Serum + GlutaMAX + IL-2 | 100% AIM-V + GlutaMAX + IL-2 |

There was no difference in the fold expansion observed for TIL expanded using no more than one type of cell culture medium as compared to TIL expanded using two types of cell culture medium. Viability and cell composition are set forth in Table 12.

TABLE 12

| Sample | Group | Viability | Phenotyping NT (not tested) | | | |
|---|---|---|---|---|---|---|
| | | | CD3 | CD3CD4 | CD3CD8 | CD56 |
| 3524 | 50/50 | 96.5% | 98.40% | 1.80% | 94.20% | 0.30% |
| | AIM-V | 97.0% | 98.10% | 1.70% | 92.00% | 0.30% |

TABLE 12-continued

| Sample | Group | Viability | Phenotyping NT (not tested) | | | |
|---|---|---|---|---|---|---|
| | | | CD3 | CD3CD4 | CD3CD8 | CD56 |
| 3546 | 50/50 | 97.7% | NT | NT | NT | NT |
| | AIM-V | 96.8% | NT | NT | NT | NT |
| 3552 | 50/50 | 96.2% | 95.60% | 21.30% | 70.50% | 0.20% |
| | AIM-V | 97.3% | 94.80% | 24.80% | 65.80% | 0.20% |

There was no difference in the viability or cell composition observed for TIL expanded using no more than one type of cell culture medium as compared to TIL expanded using two types of cell culture medium.

Potency of the TIL is measured and compared for TIL expanded using no more than one type of medium and TIL expanded using two types of medium. Effector cells ($1 \times 10^5$) are co-cultured with target cells ($1 \times 10^5$), with AK1700 used as a negative control and DM5 A2 used as a positive control. IFN-gamma secretion is measured by ELISA. There was no significant difference in IFN-gamma secretion for TIL expanded using no more than one type of cell medium as compared to TIL expanded using two types of cell medium.

Example 14

This example demonstrates that expanding the number of TIL using a higher ratio of feeders provides a higher number of TIL.

TIL ($5 \times 10^6$) from two tumor samples were expanded as described above using allogeneic feeder cells at a TIL: Feeder cell ratio of 1:100, 1:50, or 1:25. Cells were counted on days 7, 11, and 14. Viability and cellular composition were evaluated on day 14.

There was no difference in cell number between the three groups at Day 7. At Days 11 and 14, however, expansion using a higher ratio of feeder cells corresponds with a better expansion of the number of TIL ($9.9 \times 10^9$ TIL at 1:100 ratio; $8 \times 10^9$ at 1:50 ratio, and $5.8 \times 10^9$ at a 1:25 ratio at Day 14 for Sample 1 and $1.0 \times 10^{10}$ TIL at 1:100 ratio; $1.0 \times 10^{10}$ at 1:50 ratio, and $8.0 \times 10^9$ at a 1:25 ratio at Day 14 for Sample 2).

Example 15

This example demonstrates that TIL cultured in a gas permeable container have the same or better potency as compared to TIL cultured in non-gas permeable, 24 well plates.

TIL are cultured in a gas permeable container (40 mL, G-Rex10) or in a non-gas permeable, 24-well plate. Effector cells ($1 \times 10^5$) are co-cultured with target cells ($1 \times 10^5$), with AK1700 used as a negative control and DM5 A2 used as a positive control. IFN-gamma secretion is measured by ELISA. The results are shown in Table 13.

TABLE 13

|  |  | Melanoma Cell Line | | | | Tumor Samples | | | | | | |
|---|---|---|---|---|---|---|---|---|---|---|---|---|
|  |  | A2− | | A2+ | | | | | | | | |
|  | None | 888 A1,24 | 938 A1,24 | 526 A2,3 | 624 A2,3 | 2976-1,2 A3,31 | 2998 A2 | 3524 A2,25 | 3552 A1,2 | 3560 A2,23 | 3561 A1,24 | 3556 A1,66 |
| None | 0 | 0 | 0 | 0 | 0 | 12 | 10 | 0 | 0 | 0 | 0 | 0 |
| AK1700-3 | 1 | 0 | 0 | 89 | 249 | 85 | >2495 | 177 | 45 | 113 | 1 | 239 |
| DM5 | 22 | 10 | 11 | >1903 | >2527 | 66 | >1207 | 1275 | 161 | 118 | 3 | 73 |
| 3556 24 well plate | 90 | 294 | 93 | 149 | 100 | 525 | >1811 | 409 | 157 | 310 | NT | >1541 |
| 3556 G-Rex10 | 87 | 230 | 88 | 129 | 110 | 308 | >1494 | 340 | 338 | 388 | NT | >1577 |
| 3552 24 well plate | 114 | 70 | 142 | >1295 | >1763 | 184 | 621 | 627 | 139 | 149 | NT | 212 |
| 3552 G-Rex10 | 81 | 388 | >1699 | >2239 | >2470 | 363 | >1773 | >1452 | 282 | 307 | NT | 256 |
| 3560 24 well plate | 135 | 94 | 110 | 196 | 372 | 173 | 346 | 484 | 175 | 318 | NT | >1008 |
| 3560 G-Rex10 | 104 | 168 | 141 | 483 | 624 | 240 | 870 | 453 | 212 | 572 | NT | >1004 |
| 3561 24 well plate | 70 | 539 | 305 | 166 | 327 | 456 | 402 | 205 | 97 | 264 | 207 | 252 |
| 3561 G-Rex10 | 84 | 1215 | 419 | 113 | 216 | 515 | 323 | 265 | 128 | 329 | 253 | 290 |

There was no significant difference in IFN-gamma secretion for TIL cultured in gas permeable containers as compared to TIL cultured in non-gas permeable 24 well plates.

Example 16

This example demonstrates the treatment of melanoma using TIL prepared by initially culturing the TIL in gas permeable flasks and then rapidly expanding the number of TIL in gas permeable flasks. Tumor tissue samples were obtained from seven melanoma patients. The tumor tissue samples were cultured in G-Rex10 flasks. TIL were obtained from the cultured tumor tissue samples. The numbers of TIL were expanded in G-Rex100 flasks. The expanded cells were administered to the patients.

Seven patients were treated. One patient (1) had an objective response (OR) by Response Evaluation Criteria In Solid Tumors (RECIST) standards. Six patients (6) were non-responders (NR).

Example 17

This example demonstrates the treatment of melanoma using TIL prepared by expanding the number of selected TIL in gas permeable flasks.

Tumor tissue samples were obtained from 55 melanoma patients. Compete medium (2 ml) (supplemented with 6000 IU/ml IL-2) was added to the wells in the top row of each 24-well plate. A single fragment of tumor was added to each media-containing well.

TIL were obtained from the tumor tissue samples and cultured as follows. Fragments were incubated in multiwell plates in a humidified incubator at 37° C., with 5% $CO_2$ in air for 5 days without disturbance. After 5 days, the TIL cultures in plates were monitored for growth by viewing with an inverted light microscope. At this point TIL and other cell types have extravasated from the fragment and/or propagated in the wells. Half of the CM in plates was replaced with fresh CM containing IL-2 (6000 IU/ml). Media (1 ml) was aspirated, taking care not to disturb the cells on the bottom of the well, and replaced with 1 ml of fresh medium containing IL-2 (6000 CU/ml). Every 2-3 days, or approximately 3 times per week, the plates were monitored for TIL growth. When TIL expansion was evident, a sample from the well was counted to quantify cell concentration. When the culture exceeded $1 \times 10^6$ lymphocytes/ml or became nearly confluent then the well was split 1:2. Splitting was accomplished by mixing gently with a transfer pipette and transferring 1 ml of culture to a new well, then adding 1 ml of CM containing IL-2 (6000 IU/ml) to each daughter well. Fragment cultures that showed growth, up to 24 in total, were split in to 2 wells. The first 12 fragment cultures that required a second split in to 4 wells were maintained. The remaining fragment cultures were frozen as a pool 1 (PF1). Typically, 8 fragment cultures were carried through to an 8 well split and maintained for therapy. The remaining cultures were frozen as pool 2 (PF2). The fragments that were being maintained for therapy were analyzed by FACS for CD3, CD4, CD8 and CD56 content as close to the date of REP as possible.

The cultures were screened for specificity by co-culturing 100 μl of TIL with media only, autologous fresh tumor cells, or autologous fresh tumor cells and MEW Class I antibody, and IFN-γ release was measured. Reactive cultures were selected for expansion.

The numbers of TIL (from the selected cultures that released 200 pg/ml or more of IFN-γ) were expanded in G-Rex100 flasks. The expanded cells were administered to the patients.

Out of fifty-five patients treated, 18 experienced tumor regression of greater than 30% and 24 did not experience tumor regression of at least 30%. The treatment outcome of the remaining 13 patients has not yet been evaluated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of obtaining an expanded number of TIL capable of lysing cancer cells from a mammal for adoptive cell immunotherapy comprising:
    obtaining a tumor tissue sample from the mammal;
    culturing the tumor tissue sample for 14 to 15 days in a first gas permeable container containing cell medium comprising IL-2 therein to obtain tumor infiltrating lymphocytes (TIL) from the tumor tissue sample;
    co-culturing the TIL with autologous tumor cells;
    selecting TIL based on IFN-γ release upon co-culturing the TIL with the autologous tumor cells to obtain selected TIL;
    expanding the number of the selected TIL in a second gas permeable container containing cell medium comprising IL-2 and OKT3, and culturing the selected TIL with irradiated allogeneic feeder cells and/or irradiated autologous feeder cells for a period of about 14 days to obtain expanded TIL, wherein at least a portion of the expanded TIL express CD3 and CD8.

2. The method of claim 1, wherein expanding the number of TIL comprises increasing the number of TIL by at least about 1000-fold.

3. The method of claim 1, wherein expanding the number of TIL uses about $1\times10^9$ to about $4\times10^9$ allogeneic feeder cells and/or irradiated autologous feeder cells.

4. The method of claim 1, wherein expanding the number of TIL comprises feeding the cells every third or fourth day.

5. The method of claim 1, wherein the tumor tissue sample is a melanoma tumor tissue sample.

6. The method of claim 1, wherein the mammal is a human.

7. The method of claim 1, wherein expanding the number of TIL uses irradiated allogeneic feeder cells and/or irradiated autologous feeder cells at a ratio of about 1 TIL to at least about 20 to 100 feeder cells.

8. The method of claim 1, wherein the irradiated feeder cells comprise irradiated peripheral blood mononuclear cells (PBMCs).

9. The method of claim 1, wherein the tumor tissue sample is obtained from a cancer selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer.

10. The method of claim 1, further comprising seeding the TIL with $1\times10^6$ cells per container.

11. A method of obtaining an expanded number of TIL from a human for adoptive cell immunotherapy comprising:
    obtaining a tumor tissue sample from the human;
    fragmenting the tumor tissue sample into fragments;
    culturing the tumor tissue sample fragments for 14 to 15 days in a first gas permeable container containing cell medium comprising IL-2 therein to obtain tumor infiltrating lymphocytes (TIL);
    co-culturing the TIL with autologous tumor cells;
    selecting a portion of the TIL based on IFN-γ release upon co-culturing the TIL with the autologous tumor cells to obtain selected TIL;
    seeding a second gas permeable container with about $1\times10^6$ selected TIL;
    culturing the selected TIL in the second gas permeable container for a period of about 14 days, wherein the second gas permeable container comprises cell medium comprising IL-2 and OKT3, and irradiated allogeneic feeder cells at a ratio of about 1 TIL to about 50 feeder cells to obtain expanded TIL, wherein at least a portion of said expanded TIL express CD3 and CD8.

12. The method of claim 1, wherein the duration of the method is about 42 days.

13. The method of claim 11, wherein the duration of the method is about 42 days.

* * * * *